United States Patent
Lindsay et al.

(10) Patent No.: US 12,031,248 B2
(45) Date of Patent: Jul. 9, 2024

(54) MICRO- AND NANO-STRUCTURED FIBER-BASED SUBSTRATES

(71) Applicant: KIMBERLY-CLARK WORLDWIDE, INC., Neenah, WI (US)

(72) Inventors: Stephen M. Lindsay, Appleton, WI (US); Wing-Chak Ng, Roswell, GA (US); Keyur Desai, Greenville, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 746 days.

(21) Appl. No.: 17/258,563

(22) PCT Filed: Jul. 10, 2018

(86) PCT No.: PCT/US2018/041351
§ 371 (c)(1),
(2) Date: Jan. 7, 2021

(87) PCT Pub. No.: WO2020/013805
PCT Pub. Date: Jan. 16, 2020

(65) Prior Publication Data
US 2021/0292944 A1 Sep. 23, 2021

(51) Int. Cl.
*D04H 1/4291* (2012.01)
*A61F 13/51* (2006.01)
(Continued)

(52) U.S. Cl.
CPC ........... *D04H 1/4291* (2013.01); *D04H 3/018* (2013.01); *D04H 3/14* (2013.01); *D06C 23/04* (2013.01);
(Continued)

(58) Field of Classification Search
CPC ...... D06C 11/00; D06C 23/04; D04H 1/4291; D04H 3/018; D04H 3/14; A61F 13/51;
(Continued)

(56) References Cited

U.S. PATENT DOCUMENTS

| | | |
|---|---|---|
| 4,508,113 A | 4/1985 | Malaney |
| 4,568,596 A | 2/1986 | Johnson |

(Continued)

FOREIGN PATENT DOCUMENTS

| | | |
|---|---|---|
| EP | 3023526 B1 | 9/2018 |
| JP | 2006328562 A | 12/2006 |

(Continued)

OTHER PUBLICATIONS

Hao, Jiang et al., "Nano-media: New nano-photofabric for rapid imprinting of color images and covert data storage", IEEE, Aug. 18, 2014, https://ieeexplore.ieee.org/document/6968172.
(Continued)

*Primary Examiner* — Camie S Thompson
(74) *Attorney, Agent, or Firm* — KIMBERLY-CLARK WORLDWIDE, INC.

(57) ABSTRACT

A nonwoven substrate includes individual fibers each having a fiber surface and a fiber diameter, wherein a portion of the individual fibers include a micro-embossed pattern, and wherein the micro-embossed pattern includes pattern elements equal to or smaller than the fiber diameter. The pattern elements can be recessed into and/or extend out of the fiber surface, and the nonwoven substrate can include polypropylene or polyethylene. A disposable absorbent article includes a nonwoven substrate having individual fibers each having a fiber surface and a fiber diameter, wherein a portion of the individual fibers include a micro-embossed pattern, and wherein the micro-embossed pattern includes pattern elements equal to or smaller than the fiber diameter.

16 Claims, 3 Drawing Sheets

(51) Int. Cl.
    *D04H 3/018*     (2012.01)
    *D04H 3/14*     (2012.01)
    *D06C 23/04*     (2006.01)

(52) U.S. Cl.
    CPC ........ *A61F 13/51* (2013.01); *D10B 2321/021* (2013.01); *D10B 2321/022* (2013.01); *D10B 2401/021* (2013.01); *D10B 2401/041* (2013.01); *D10B 2509/026* (2013.01)

(58) Field of Classification Search
    CPC ............... A61F 13/15; A61F 13/15203; A61F 13/51104; A61F 13/5118; D10B 2321/021; D10B 2321/022; D10B 2401/021; D10B 2401/041; D10B 2509/026; B32B 2307/73
    USPC .............................................. 442/327; 26/28
    See application file for complete search history.

(56) References Cited

U.S. PATENT DOCUMENTS

| | | | |
|---|---|---|---|
| 5,017,423 | A | 5/1991 | Bossmann et al. |
| 5,143,774 | A | 9/1992 | Cancio et al. |
| 5,674,587 | A | 10/1997 | James et al. |
| 6,719,742 | B1 | 4/2004 | McCormack et al. |
| 6,911,573 | B2 | 6/2005 | Chen et al. |
| 7,213,309 | B2 | 5/2007 | Wang et al. |
| 7,413,629 | B2 | 8/2008 | Fisher et al. |
| 7,772,456 | B2 | 8/2010 | Zhang et al. |
| 8,241,543 | B2 | 8/2012 | Hugh |
| 8,283,021 | B2 | 10/2012 | Ashida et al. |
| 8,545,976 | B2 | 10/2013 | Manifold et al. |
| 9,243,368 | B2 | 1/2016 | Mellin et al. |
| 2006/0154548 | A1 | 7/2006 | Sheehan et al. |
| 2006/0286886 | A1 | 12/2006 | Komura et al. |
| 2008/0318004 | A1 | 12/2008 | Ruhe et al. |
| 2009/0155325 | A1 | 6/2009 | Wenzel et al. |
| 2010/0121304 | A1 | 5/2010 | Zhou et al. |
| 2013/0172927 | A1 | 7/2013 | Natarajan et al. |
| 2014/0141203 | A1 | 5/2014 | Sartini et al. |
| 2014/0170922 | A1 | 6/2014 | Poruthoor et al. |
| 2014/0271754 | A1 | 9/2014 | Blaney et al. |
| 2016/0091635 | A1 | 3/2016 | Ibuki et al. |
| 2016/0106633 | A1 | 4/2016 | Nagata et al. |
| 2016/0145810 | A1 | 5/2016 | Miller, IV et al. |

FOREIGN PATENT DOCUMENTS

| | | |
|---|---|---|
| KR | 20100041591 A | 4/2010 |
| WO | 10021572 A1 | 2/2010 |
| WO | 16022880 A1 | 2/2016 |

OTHER PUBLICATIONS

Makansi, Munzer Dr., et al, "Holographic embossed fabrics patents on offer", Holography News, Dec. 2001, http://dialog.proquest.com/professional/docview/1091106561?accountid=157282.

Hafeez, Hassan et al., "Novel one-step route to induce long-term lotus leaf-like hydrophobicity in polyester fabric", Journal of Adhesion Science and Technology, 2015, http://dialog.proquest.com/professional/docview/1696772270?accountid=157282.

MICRO- AND NANO-STRUCTURED FIBER-BASED SUBSTRATES

BACKGROUND

The present disclosure relates to a process for preparing fiber-based surfaces, such as nonwoven surfaces, that exhibit enhanced properties such as hydrophobic properties, without the addition of a chemical treatment.

A hydrophobic surface exhibits a sessile water contact angle of from about 90° to about 120°. If, additionally, the surface exhibits a water droplet roll-off (sliding) angle of less than 10°, the surface is deemed to be "self-cleaning." Most man-made materials such as fabrics, nonwovens, cellulose tissues, polymer films, etc., do not have surfaces with such properties. Currently, there are several methods to modify a non-hydrophobic surface to achieve hydrophobicity. One method is to graft hydrophobic polymer(s) (using a monomer, co-monomers, etc.) onto every exposed surface of a non-hydrophobic material. Such a method makes the material hydrophobic throughout the thickness of the material, which might not be desired in most cases. It is also not cost effective, cannot be used for a continuous production, and can lead to undesirable environment issues.

Another method of achieving enhanced properties, such as enhanced hydrophobicity, includes the application of a chemical treatment to the surface. Various fluorinated and non-fluorinated formulations, both water- and solvent-based, have been attempted for achieving hydrophobicity. Over the past several decades, many approaches to these hydrophobic surfaces have been developed that commonly require harsh organic solvents, complex processing methods, and/or environmentally undesirable fluorinated chemistry. In addition, many of the demonstrated methods are not relevant in practice on large scales in commercial application, not only for their negative consequences to the environment, but also the inability to economically prepare large-area fluid repellent surfaces at sufficiently low-cost. Imparting liquid repellency via large-area approaches, such as spray-casting or size press coating, have been shown to be viable for low-cost and substrate-independent fluid management.

A standard approach is to coat a specially-formulated liquid dispersion onto a surface. Upon subsequent drying, a nano-structured hydrophobic film forms. To use such an approach, the deposited film must exhibit a chemical and physical morphology characteristic of hydrophobic surfaces. First, the formulation requires at least one low-surface energy (i.e., hydrophobic) component, and second, the treated surface has to have a rough surface texture, preferably extending over several length-scales characteristic of micro- and/or nano-roughness.

Low-cost, large-area hydrophobicity-inducing methods are of great value to many applications requiring a passive means for attaining efficient liquid repellency. While many applications are envisioned, only few are realizable due to either the high-cost or low-durability of such treatments. Recently, spray deposition of polymer-particle dispersions has been demonstrated as a means for producing low-cost, large-area, durable, hydrophobic composite coatings/films; however, the dispersions used for spray deposition of hydrophobic coatings generally contain harsh or volatile solvents. Solvents are required for wet processing of, for example, polymers, as well as for dispersing hydrophobic nanoparticles, thus inhibiting scalability due to the increased cost in chemical handling and safety concerns. This problem can be overcome by replacing solvents with water, but this situation is paradoxical: producing a highly water-repellent coating from an aqueous dispersion.

Also, such coatings usually contain fluoropolymers. A low-surface energy fluoropolymer (e.g., fluoroacrylic copolymers, poly(tetrafluoroethylene), etc.) is typically incorporated into the formulation to achieve liquid repellency. However, concerns over their bio-persistence have provided an impetus for eliminating these chemicals. The problems with the byproducts of fluoropolymer degradation, for example long-chain perfluorinated acids (PFAs) that have a documented ability to bioaccumulate, as well as the potential adverse effects PFA in maternal concentrations can have on human offspring, have led to a shift in the manufacture and usage of fluoropolymers. One common PFA of particular concern is perfluorooctanoic acid (PFOA). In 2006, the EPA (United States Environmental Protection Agency) introduced its PFOA (perfluorooctanoic acid) Stewardship Program and invited eight major fluoropolymer and telomer manufacturers to commit to eliminating precursor chemicals that can break down into PFOA; in one case, DuPont has since introduced so-called short-chain chemistry, whereby the length of perfluorinated chains within polymers are kept below a threshold to avoid degradation into PFOA. In other applications, usage of fluoropolymers in products that come in sustained contact with the human body or in disposable items intended for landfilling after consumption must be minimized.

SUMMARY

Using a mechanical instead of a chemical process eliminates the need for fluorinated compounds, organic solvents, and other potentially harmful and/or expensive chemicals. This novel, environmentally-friendly process is herein characterized as having potential in numerous fluid management applications by virtue of its simplicity, efficiency, and versatility. For a multitude of safety, health, economic, and environmental issues, it is important that the process be independent of any liquid treatments.

The disclosure is directed to a nonwoven substrate including individual fibers each having a fiber surface and a fiber diameter, wherein a portion of the individual fibers include a micro-embossed pattern, and wherein the micro-embossed pattern includes pattern elements equal to or smaller than the fiber diameter.

In an alternative aspect, the disclosure is directed to a nonwoven substrate including individual fibers each having a fiber surface and a fiber diameter, wherein a portion of the individual fibers include a micro-embossed pattern, wherein the micro-embossed pattern includes pattern elements equal to or smaller than the fiber diameter, wherein the pattern elements are recessed into and/or extend out of the fiber surface, and wherein the nonwoven substrate includes polypropylene or polyethylene.

In another aspect, the disclosure is directed to a disposable absorbent article including a nonwoven substrate having individual fibers each having a fiber surface and a fiber diameter, wherein a portion of the individual fibers include a micro-embossed pattern, and wherein the micro-embossed pattern includes pattern elements equal to or smaller than the fiber diameter.

BRIEF DESCRIPTION OF THE FIGURES

The foregoing and other features and aspects of the present disclosure and the manner of attaining them will become more apparent, and the disclosure itself will be better understood by reference to the following description, appended claims and accompanying drawings, where:

Figure 1:
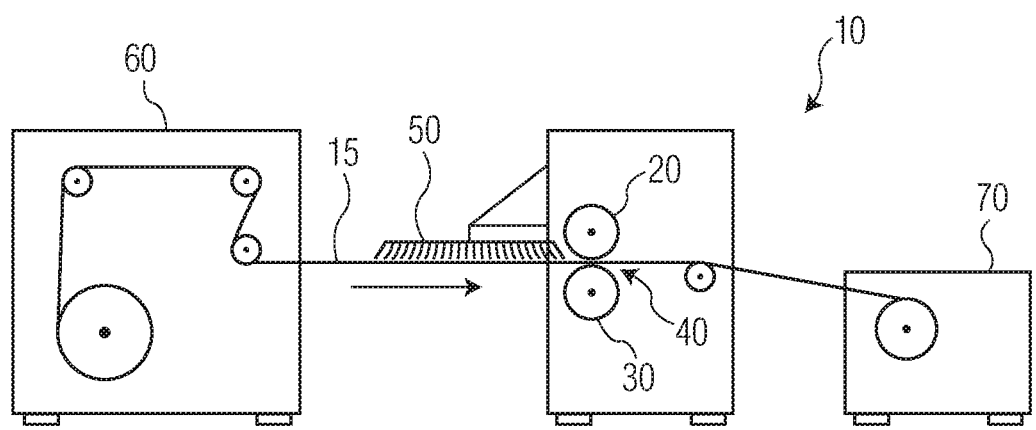
FIG. 1 schematically illustrates the micro- and nano-embossing process of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

All percentages are by weight of the total solid composition unless specifically stated otherwise. All ratios are weight ratios unless specifically stated otherwise.

The term "superhydrophobic" refers to the property of a surface to repel water very effectively. This property is quantified by a water contact angle exceeding 150°.

The term "hydrophobic," as used herein, refers to the property of a surface to repel water with a water contact angle from about 90° to about 120°.

The term "hydrophilic," as used herein, refers to surfaces with water contact angles well below 90°.

The term "self-cleaning," as used herein, refers to the property to repel water with the water roll-off angle on a tilting surface being below 10°.

The term "fiber-based" substrate refers to any substrate that is fully or partially made of fibers (i.e. the substrate includes or is composed of fibers and in one aspect consists of fibers). Corresponding substrates are known in the art and examples thereof represent nonwovens, wovens, knitted fabrics, or rowings. Preferably, the fiber-based substrate is a nonwoven substrate. The fibers of the fiber-based substrate are not particularly limited and can, for example, be polymer fibers or fibers made of composite materials, such as multicomponent fibers and nanocomposite fibers. The fibers of the fiber-based substrate are preferably polymer fibers.

As used herein, the term "nonwoven web" or "nonwoven fabric" means a web having a structure of individual fibers or threads that are interlaid, but not in an identifiable manner as in a knitted web. Nonwoven webs have been formed from many processes, such as, for example, meltblowing processes, spunbonding processes, air-laying processes, coforming processes and bonded carded web processes. The basis weight of nonwoven webs is usually expressed in ounces of material per square yard (osy) or grams per square meter (gsm) and the fiber diameters are usually expressed in microns, or in the case of staple fibers, denier. It is noted that to convert from osy to gsm, osy must be multiplied by 33.91.

As used herein the term "spunbond fibers" refers to small diameter fibers of molecularly oriented polymeric material. Spunbond fibers can be formed by extruding molten thermoplastic material as fibers from a plurality of fine, usually circular capillaries of a spinneret with the diameter of the extruded fibers then being rapidly reduced as in, for example, U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al., and U.S. Pat. No. 5,382,400 to Pike et al. Spunbond fibers are generally not tacky when they are deposited onto a collecting surface and are generally continuous. Spunbond fibers are often about 10 microns or greater in diameter. However, fine fiber spunbond webs (having an average fiber diameter less than about 10 microns) can be achieved by various methods including, but not limited to, those described in commonly assigned U.S. Pat. No. 6,200,669 to Marmon et al. and U.S. Pat. No. 5,759,926 to Pike et al.

As used herein, the term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, the term "multicomponent fibers" refers to fibers or filaments that have been formed from at least two polymers extruded from separate extruders but spun together to form such fibers. Multicomponent fibers are also sometimes referred to as "conjugate" or "bicomponent" fibers or filaments. The term "bicomponent" means that there are two polymeric components making up the fibers. The polymers are usually different from each other, although conjugate fibers can be prepared from the same polymer, if the polymer in each state is different from the other in some physical property, such as, for example, melting point, glass transition temperature or the softening point. In all cases, the polymers are arranged in purposefully positioned distinct zones across the cross-section of the multicomponent fibers or filaments and extend continuously along the length of the multicomponent fibers or filaments. The configuration of such a multicomponent fiber can be, for example, a sheath/core arrangement, wherein one polymer is surrounded by another, a side-by-side arrangement, a pie arrangement or an "islands-in-the-sea" arrangement. Multicomponent fibers are taught in U.S. Pat. No. 5,108,820 to Kaneko et al.; U.S. Pat. No. 5,336,552 to Strack et al.; and U.S. Pat. No. 5,382,400 to Pike et al. For two component fibers or filaments, the polymers can be present in ratios of 75/25, 50/50, 25/75 or any other desired ratios.

As used herein, the term "substantially continuous fibers" is intended to mean fibers that have a length that is greater than the length of staple fibers. The term is intended to include fibers that are continuous, such as spunbond fibers, and fibers that are not continuous, but have a defined length greater than about 150 millimeters.

As used herein, the term "staple fibers" means fibers that have a fiber length generally in the range of about 0.5 to about 150 millimeters. Staple fibers can be made of the above-mentioned materials for the fibers of the fiber-based substrate and can, for example, be cellulosic fibers or non-cellulosic fibers. Some examples of suitable non-cellulosic fibers that can be used include, but are not limited to, polyolefin fibers, polyester fibers, nylon fibers, polyvinyl acetate fibers, and mixtures thereof. Cellulosic staple fibers include for example, pulp, thermomechanical pulp, synthetic cellulosic fibers, modified cellulosic fibers, and the like.

Cellulosic fibers can be obtained from secondary or recycled sources. Some examples of suitable cellulosic fiber sources include virgin wood fibers, such as thermomechanical, bleached and unbleached softwood and hardwood pulps. Secondary or recycled cellulosic fibers can be obtained from office waste, newsprint, brown paper stock, paperboard scrap, etc. Further, vegetable fibers, such as abaca, flax, milkweed, cotton, modified cotton, cotton linters, can also be used as the cellulosic fibers. In addition, synthetic cellulosic fibers such as, for example, rayon and viscose rayon can be used. Modified cellulosic fibers are generally composed of derivatives of cellulose formed by substitution of appropriate radicals (e.g., carboxyl, alkyl, acetate, nitrate, etc.) for hydroxyl groups along the carbon chain.

As used herein, the term "pulp" refers to fibers from natural sources, such as woody and non-woody plants. Woody plants include, for example, deciduous and coniferous trees. Non-woody plants include, for example, cotton, flax, esparto grass, milkweed, straw, jute, hemp, and bagasse.

As used herein, the term "disposable absorbent products" refers to diapers, training pants, absorbent underpants, adult incontinence products, sanitary wipes, and feminine hygiene products, such as sanitary napkins, pads, liners, and tampons, and other similar products. Disposable absorbent products includes absorbent medical products, which include products such as medical bandages, tampons intended for medical, dental, surgical, and/or nasal use, surgical drapes and garments, coverings in medical settings, and the like.

Prior art formulations used to prepare a substrate to demonstrate hydrophobicity can require harmful fluorinated polymers in conjunction with solvents that include harmful volatile organic compounds (VOCs). The present disclosure solves these problems for these applications by eliminating the need for any chemical treatments of the substrate to minimize the use of harmful VOCs, a common, non-trivial problem with coatings aiming to achieve hydrophobicity upon deposition.

The present disclosure describes a pattern impressed on the fibers of a fiber-based substrate, preferably a nonwoven substrate, using a thermomechanical process for the formation of a surface having enhanced properties, such as an enhanced hydrophobic surface. The fiber-based substrate has a micro- or nano-structure imprinted into the fibers after the initial forming of the substrate. The micro- or nano-structure has a feature size that is smaller than the fiber diameter, such that the structures can be resolved on individual fibers on the surface of the substrate. The pattern is imprinted into the fiber surface while largely retaining the porosity, thickness, and softness (lack of rigidity) of the fiber-based, preferably nonwoven, substrate. The microstructures confer functional benefit such as elevated contact angle.

A hydrophobic surface of the present disclosure can be produced on a fiber-based substrate, preferably a nonwoven substrate, by employing a micro- or nano-embossing process that impresses a sub-fiber-width pattern on the fibers of that substrate.

For liquid-repellent functionality, specifically to water, the surface requires low surface energies and a suitable degree of roughness to reduce the liquid-to-solid interfacial contact area, thus increasing the contact angle of water droplets used as a measure of surface wettability. The wettability of a smooth un-textured surface in an air environment is determined by the free surface energies of the liquid and solid being introduced; whether the surface is hydrophobic or hydrophilic, the interaction with water is tunable via the surface roughness imparted by the imposition of micro- or nano-patterns. A high-degree of surface roughness modifies the intrinsic wettability of the surface into hydrophobicity, or having a contact angle to water of about 90° to about 120°.

In practice until recently, the fabrication of super-repellent composites requiring polymers with sufficiently low surface energies (i.e., for repelling water, $\gamma < 72$ mN/m) demanded the use of harsh solvents for wet-processing, thus hindering the development of entirely water-based systems. Fluorine-free and water-compatible polymer systems capable of delivering low surface energy have been the primary challenge for the development of truly environmentally-benign superhydrophobic coatings. A low surface energy, water-borne fluoropolymer dispersion (DuPont Capstone ST-100) was used in a water-based superhydrophobic spray, where the correlation between contact angle and hydrostatic resistance was studied, but again, the presence of fluorinated compounds in the composite still posed environmental concerns. At one point the EPA initiated a reduction in the manufacture of many dangerous fluoropolymer compounds; such compounds have a high risk of breaking down into perfluorooctanoic acids (PFOA) and can have an extremely adverse environmental impact. PFOA, a known cause of birth defects, can enter into ground water, polluting reservoirs and aquatic wild-life, eventually being ingested by humans where it can accumulate to hazardous levels. Although short-chain fluoropolymers made in response to the EPA initiative, such as DuPont's Capstone ST-100, are available and pose less environmental risk; eliminating the necessity of fluorine altogether for repellency has been a primary goal of this work. The methods described herein have the potential to create surfaces having enhanced properties, such as hydrophobic surfaces for example, without the use of fluorinated composites, organic solvents, or other chemicals. In that respect, the methods described herein are a more environmentally-conscious, so-called "green" alternative.

Choosing patterns having nano-scale dimensions allows for fine control over surface roughness and a greater reduction in the liquid-to-solid interfacial contact area; for hydrophobic, or low-surface energy surfaces, this translates into an increased resistance to fluid wetting by allowing the solid surface to retain pockets of vapor that limit liquid/solid contact.

The present disclosure relates to a surface of a substrate, or the substrate itself, exhibiting enhanced characteristics, such as hydrophobic characteristics, when a thermomechanical patterning process is applied. The enhanced characteristics, such as hydrophobicity, can be applied either over the entire surface or patterned throughout or on the substrate material. Further examples of potential benefits from surface structuring include modification of wetting and fluid handling properties, friction, adhesion, tactile properties, optical effects, and anti-microbial effects.

In a particular aspect, the fiber-based substrate, for example a nonwoven substrate, is made of a thermoplastic polymer (for example, polypropylene) and the pattern is imprinted by means of roll-to-roll embossing, such as continuous roll-to-roll micro-hot embossing, roll-to-roll thermal nanoimprint, roll-to-roll soft embossing and discontinuous micro/nano hot embossing, thermal nanoimprint, soft embossing. The fiber-based substrate itself is formed by processes well known to those skilled in the art. If a fiber-based substrate such as a nonwoven substrate includes melt-bonded points, these melt-bonded points can be formed prior to embossing, or the embossing pattern and the bond pattern can be incorporated into the same roll and process. The bond points are typically at least an order of magnitude larger than the much finer micro- and nano-embossed features.

In another aspect illustrated in FIG. 1, the present disclosure relates to a patterning apparatus 10, including a pattern roll 20 and a pressure roll 30 forming a nip 40, wherein the pattern roll 20 includes protrusions or grooves having a diameter being smaller than a diameter of fibers included in a fiber-based substrate 15, preferably a nonwoven substrate, introduced into the nip 40 for roll-to-roll (micro-hot) embossing. The statements and definitions given with respect to the other aspects of the present disclosure, when not differing from the following statements and definitions, analogously apply to this aspect of the present disclosure.

According to the present disclosure, the pattern roll 20 includes protrusions or grooves having a diameter being smaller than the diameter of the fibers included in the fiber-based substrate 15 as used in the present disclosure. The shape, diameter and further dimensions of the protrusions or grooves and the spaces between the protrusions or grooves are not particularly limited, with the exception that the protrusions or grooves have a diameter being smaller than the diameter of the fibers included in the substrate 15. For example, the protrusions or grooves each can have a diameter/length of the edge of 20 µm or less, more particularly from 5.0 nm to 20 µm. Moreover, the protrusions or grooves can have the shapes of, for example, pins, such as cylindrical pins, triangular pins, square pins, polygonal pins, cylinders, and star-shaped pins, pipe-like cross-sectional shapes (also circular, square etc.), all preferably 2.5D, cones, pyramids, 3D bell-shaped curves, free formed surfaces, statistical surfaces (sandblasted, self-assembled, random etc.), and combinations of the same. Moreover, the spaces between the protrusions or grooves each can be 20 µm or less, more particularly from 5.0 nm to 20 µm.

The material of the pattern roll 20 and the pressure roll 30 is not particularly limited. All the rolls known to a person skilled in the art can thus be used. For example, rolls made of polymers, cotton, felt, rubber, ceramics, compounds, composite materials, combinations of different materials, such as fiber-reinforced silicon materials or fiber-reinforced foamed materials or the like, or metal or combinations of said materials can be used. The rolls can be coated with a non-stick or other suitable coating. Moreover, the rolls/structures can be covered with another material as the roll material. Accordingly, the micro- or nano-pattern (i.e. the protrusions or grooves) of the pattern roll 20 can be included in the roll material itself or can be included in a material/tool, which is wrapped around the pattern roll 20. For example, in a corresponding process, a master micro- or nano-pattern can first be fabricated by processes well known by those skilled in the art, often from a polymeric material. Typically, a more durable tool can then be created from the fabricated master by well-known processes, including nickel electroplating. This durable tool can be a thin shim, a carbon tool, a tool made of a high performance polymer, such as PEEK, a tool made of composite materials, or a tool made of combinations of materials, and that is wrapped around the pattern roll 20.

In a preferred aspect, the pressure roll 30 is made of a material selected from an elastomeric material, such as silicon-based elastomers, non-silicon-based elastomers, foamed elastomers, and thermoplastic elastomers, and felt, preferably from a silicone rubber and felt, more preferably from a felt material. Micro-hot embossing was developed primarily for films. A common challenge with micro-hot embossing of fiber-based substrates, such as nonwoven substrates, is that the pressure and heat required to imprint a pattern into the fiber surface can also result in crushing the fiber structure, flattening the fibers, and/or fusing the fibers together. This can destroy the permeability, caliper, and softness of the material, in some cases even melting the substrate into a film. In case the pressure roll 30 is made of a soft/elastomeric material such side-effects can be reduced and even be overcome.

The felt material is not particularly limited and can, for example, be wool felt material. Preferably, the felt material is an uncarbonized wool felt material.

The apparatus can further include means for loosening the fibers of the fiber-based substrates 15, such as a nonwoven substrate, after it has been introduced into the nip 40. This can increase the loft and caliper and thus further reduce the above-mentioned side-effects. Loosening can be performed, for example, by using a ring rolling process or by any other suitable process known in the art. This loosening step reverses the potential negative effects of the embossing nip 40.

The pattern roll 20 and/or the pressure roll 30 can be heated and/or the fiber-based substrate can be preheated in an optional preheating unit 50 (see FIG. 1) before being introduced into the nip 40. Suitable means for heating the rolls and/or suitable preheating units (e.g., radiative, conductive, convective) are known in the art. For example, the preheating unit 50 can be IR heaters. For example, the substrate 15 can be heated by both the preheating unit 50 and the roll(s) 20, 30, can be heated with the preheating unit 50 and cooled with the roll(s) 20, 30, or can be heated only with the roll(s) 20, 30.

Furthermore, it is also possible to use several heating and cooling rolls. The temperature/energy being applied to the substrate 15 depends on the material of the fiber-based substrate 15 and the desired structure. For example, a polymeric fiber-based substrate 15 can be heated to a temperature close to the glass transition temperature, such as TG+20° C., or the softening range of the polymeric material. The glass transition temperature can be determined for example via DSC (differential scanning calorimetry) and DMA (Dynamic mechanical analysis). Although the temperature/energy being applied to the substrate 15 depends on the material of the fiber-based substrate 15 and the desired structure the temperature applied to the fiber-based substrate 15, such as a nonwoven substrate, can be from 30 to 350° C., preferably from 60 to 150° C., more preferably from 80 to 120° C., and most preferably from 85 to 110° C.

The pressure roll 30 and the pattern roll 20 are brought together under pressure to form the nip 40. The substrate 15 is brought to the nip 40 where the micro- or nano-pattern on the pattern roll 20 is imprinted into the substrate 15 by means of pressure and heat. The pressure being applied to the substrate 15 is not particularly limited. For example, the pressure can be from 10 to 100000 N, preferably from 4000 to 50000 N, more preferably from 5000 to 20000 N, most preferably from 5000 to 10000 N, at for example a 100 mm substrate width when using a felt pressure roll 30.

In other aspects, suitable processes include serial (not continuous) hot embossing, roll-to-plate hot embossing, and nano-imprint lithography, in which the pattern is formed in a UV-cured printed coating. In addition, other coatings can be applied to the substrate 15 prior to imprinting.

Further parts that can be included in the apparatus such as storage and transport means (for the treated and untreated substrate) in the form of unwinder 60 and upwinder 70 units as depicted in FIG. 1, any other suitable storage means, and conveyors or other transport means as are known in the art.

The fiber-based substrate 15 can undergo embossing as well as the optional preheating and loosening more than once. For this purpose, the substrate can be subjected to the same pattern and pressure rolls 20, 30, optional preheating unit 50, and optional loosening means or to further installations of the corresponding means, which can be the same or which can differ from the first installations. The loosening step twists and re-arranges the fibers of the fiber-based substrate, in some cases exposing new fibers to the surface. As a result, carrying out embossing and loosening more than once can produce an end product with fibers imprinted on both the top and sides of a fiber, and imprinted fibers can end up not only at the surface but also in front of or behind other imprinted fibers, and can create a more robustly-patterned material.

Preferably, the embossing step as well as the optional preheating and loosening is carried out at least once, more preferably at least twice, more preferably at least three times, more preferably at least four times.

The fiber-based substrate can also be embossed on both sides (opposite surfaces) of the substrate 15, simultaneously in one embossing step or when subjecting the substrate 15 to multiple embossing steps (including, for example, turning the substrate).

The fiber-based substrate 15, such as a nonwoven substrate, as used in the present disclosure is introduced into the nip 40. In a preferred aspect, the fibers of the substrate 15 include a polymer, preferably a thermoplastic polymer. More preferably, the thermoplastic polymer is selected from polypropylene and/or polyethylene. Preferably, the fibers of the substrate 15 have diameter of 50 µm or less, more particularly from 1.0 nm to 50 µm, 10 nm to 50 µm, 100 nm to 50 µm, 100 nm to 40 µm, 100 nm to 35 µm, 500 nm to 35 µm, and from 1.0 µm to 25 µm.

If the fiber-based substrate 15, such as a nonwoven substrate, includes melt-bonded points, these melt-bonded points can be formed prior to embossing, or the embossing pattern and the bond pattern can be incorporated into the same roll and process. The bond points are typically at least an order of magnitude (i.e. at least by the factor of 10) larger than the much finer micro- and nano-embossed features. Means for forming melt-bonded points are known in the art and can be included in the apparatus of the present disclosure. For example, such means include thermal calendaring bonding, ultrasonic bonding, and pressure bonding.

The micro-structures embossed on the fiber-based substrate 15 confer functional benefits such as an elevated contact angle. For example, the contact angle of the treated substrate is increased by at least 5°, in particular by at least 10°, when compared to the untreated substrate. For example, the contact angle of the treated substrate 15 is at least 110°, in particular at least 128°.

In a preferred aspect, the micro-embossed pattern on the fiber-based substrate 15, such as a nonwoven substrate, has a pattern roughness of more than 1.5, more preferably of more than 1.7, more preferably of more than 2.3, more preferably of more than 3.0. Pattern roughness is the roughness ratio of the embossed regions of the fiber surface. Roughness ratio is the ratio between the actual and projected solid surface area (r=1 for smooth surface, r>1 for rough surface). This is the roughness value used in the Wenzel and Cassie-Baxter wetting equations. Characterization was done using a Keyence laser confocal microscope with a 50 or 100× objective lens, showing the embossed pattern in sufficient resolution. Three or four characteristic fiber regions containing pattern were selected. VK Analyzer software from Keyence was used to automatically identify the 3D surface area and 2D projected area of the selection. The ratio of these two values is the roughness ratio. The average of these selections was used for the pattern roughness value.

Preferably, the treated fiber-based substrate 15, such as a nonwoven substrate, has a substrate density of less than 0.12 $g/cm^3$, more preferably less than 0.1 $g/cm^3$, and even more preferably less than 0.09 $g/cm^3$.

The pattern coverage can be selected as needed for the corresponding application of the substrate 15. Accordingly, low to high pattern coverage can be obtained with the present disclosure. In a preferred aspect, the pattern coverage is at least 20%, more preferably at least 40%, more preferably at least 60%, and most preferably at least 70% based on the projected fiber surface area visible from above.

Pattern coverage was measured using digital image analysis. An optical microscope with a 20× objective lens was used to acquire images, with resolution sufficient to determine which areas of the visible fiber surface contained embossed patterns. Pattern coverage is defined as the number of pixels identified as containing pattern in an image divided by the total number of pixels identified as containing fiber in the same image. "Pattern" regions were identified using an edge detection method to identify only the high contrast areas of the image corresponding to embossed patterns. "Fiber" regions were identified based on the brightness of the image.

In another aspect, the present disclosure relates to a patterning process including the step of (a) subjecting a fiber-based substrate 15, preferably a nonwoven substrate, to roll-to-roll (micro-hot) embossing by introducing the substrate into a nip 40 provided by a pattern roll 20 and a pressure roll 30, wherein the pattern roll 20 includes protrusions or grooves having a diameter being smaller than the diameter of fibers included in the substrate 15. The statements and definitions given with respect to the other aspects of the present disclosure, when not differing from the following statements and definitions, analogously apply to this aspect of the present disclosure. In a preferred aspect, the patterning apparatus according to the present disclosure is used for carrying out the patterning process.

Preferably, the patterning process further includes the step of ($a_0$) preheating the substrate 15 before the step (a). As mentioned with respect to the apparatus, said preheating step can be carried out with a respective preheating unit 50. The substrate 15 can also or alternatively be heated or cooled by the pattern roll 20 and/or the pressure roll 30 or other additional rolls.

In a preferred aspect, the patterning process further includes the step of (b) loosening the fibers of the substrate 15 after the step (a). As mentioned with respect to the apparatus, said loosening step can be carried out with respective loosening means.

Furthermore, the step (a) as well as the optional steps ($a_0$) and (b) can be carried out in the given order at least once, preferably at least twice, more preferably at least three times, more preferably at least four times.

In one aspect, the patterning process further includes the step of forming melt-bonded points before or during the step (a) in the fiber-based substrate 15, such as a nonwoven substrate.

Following the processes described herein, the micro- or nano-patterned fiber-based substrate 15 has increased surface roughness resulting in greater hydrophobicity. In other aspects, the micro- or nano-structure could impart additional benefits to the fiber-based substrate 15, including but not limited to changes in friction, adhesion, tactile properties, optical effects, and/or anti-microbial effects.

In some aspects of the present disclosure, the substrate 15 that is treated is a nonwoven web. Suitable substrates of the present disclosure can include a nonwoven fabric and laminates of nonwoven fabrics. The substrate 15 can also be a tissue or towel, as described herein, provided the tissue or towel includes a thermoplastic synthetic component. Materials and processes suitable for forming such substrates are generally well known to those skilled in the art. For instance, some examples of nonwoven fabrics that can be used in the present disclosure include, but are not limited to, spunbonded webs, meltblown webs, bonded carded webs, airlaid webs, coform webs, spunlace nonwoven webs, hydraulically entangled webs, and the like. In each case, at least one of the fibers used to prepare the nonwoven fabric is a thermoplastic-material-containing fiber. In addition, nonwoven fabrics can be a combination of thermoplastic fibers and natural fibers, such as, for example, cellulosic fibers (softwood pulp, hardwood pulp, thermomechanical pulp, etc.). Generally, from the standpoint of cost and desired properties, the substrate 15 of the present disclosure is a nonwoven fabric.

If desired, the nonwoven fabric can also be bonded using techniques well known in the art to improve the durability, strength, hand, aesthetics, texture, and/or other properties of the fabric. For instance, the nonwoven fabric can be thermally (e.g., pattern bonded, through-air dried), ultrasonically, adhesively and/or mechanically (e.g., needled) bonded. For instance, various pattern bonding techniques are described in U.S. Pat. No. 3,855,046 to Hansen; U.S. Pat. No. 5,620,779 to Levy, et al.; U.S. Pat. No. 5,962,112 to Haynes, et al.; U.S. Pat. No. 6,093,665 to Sayovitz, et al.; U.S. Design Patent No. 428,267 to Romano, et al.; and U.S. Design Patent No. 390,708 to Brown.

The nonwoven fabric can be bonded by continuous seams or patterns. As additional examples, the nonwoven fabric can be bonded along the periphery of the sheet or simply across the width or cross-direction (CD) of the web adjacent the edges. Other bond techniques, such as a combination of thermal bonding and latex impregnation, can also be used. Alternatively and/or additionally, a resin, latex or adhesive can be applied to the nonwoven fabric by, for example, spraying or printing, and dried to provide the desired bonding. Still other suitable bonding techniques can be described in U.S. Pat. No. 5,284,703 to Everhart, et al., U.S. Pat. No. 6,103,061 to Anderson, et al., and U.S. Pat. No. 6,197,404 to Varona.

In another aspect, the substrate 15 of the present disclosure is formed from a spunbonded web containing monocomponent and/or multicomponent fibers. Multicomponent fibers are fibers that have been formed from at least two polymer components. Such fibers are usually extruded from separate extruders but spun together to form one fiber. The polymers of the respective components are usually different from each other, although multicomponent fibers can include separate components of similar or identical polymeric materials. The individual components are typically arranged in distinct zones across the cross-section of the fiber and extend substantially along the entire length of the fiber. The configuration of such fibers can be, for example, a side-by-side arrangement, a pie arrangement, or any other arrangement.

When used, multicomponent fibers can also be splittable. In fabricating multicomponent fibers that are splittable, the individual segments that collectively form the unitary multicomponent fiber are contiguous along the longitudinal direction of the multicomponent fiber in a manner such that one or more segments form part of the outer surface of the unitary multicomponent fiber. In other words, one or more segments are exposed along the outer perimeter of the multicomponent fiber. For example, splittable multicomponent fibers and methods for making such fibers are described in U.S. Pat. No. 5,935,883 to Pike and U.S. Pat. No. 6,200,669 to Marmon, et al.

The substrate 15 of the present disclosure can also contain a coform material. The term "coform material" generally refers to composite materials including a mixture or stabilized matrix of thermoplastic fibers and a second non-thermoplastic material. As an example, coform materials can be made by a process in which at least one meltblown die head is arranged near a chute through which other materials are added to the web while it is forming. Such other materials can include, but are not limited to, fibrous organic materials, such as woody or non-woody pulp such as cotton, rayon, recycled paper, pulp fluff and also superabsorbent particles, inorganic absorbent materials, treated polymeric staple fibers and the like. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.

Additionally, the substrate 15 can also be formed from a material that is imparted with texture on one or more surfaces. For instance, in some aspects, the substrate 15 can be formed from a dual-textured spunbond or meltblown material, such as described in U.S. Pat. No. 4,659,609 to Lamers, et al. and U.S. Pat. No. 4,833,003 to Win, et al.

In one particular aspect of the present disclosure, the substrate 15 is formed from a hydroentangled nonwoven fabric. Hydroentangling processes and hydroentangled composite webs containing various combinations of different fibers are known in the art. A typical hydroentangling process uses high pressure jet streams of water to entangle fibers and/or filaments to form a highly-entangled consolidated fibrous structure, for example a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Boulton. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al.

Of these nonwoven fabrics, hydroentangled nonwoven webs with staple fibers entangled with thermoplastic fibers is especially suited as the substrate 15. In one particular example of a hydroentangled nonwoven web, the staple fibers are hydraulically entangled with substantially continuous thermoplastic fibers. The staple can be cellulosic staple fiber, non-cellulosic stable fibers or a mixture thereof. Suitable non-cellulosic staple fibers includes thermoplastic staple fibers, such as polyolefin staple fibers, polyester staple fibers, nylon staple fibers, polyvinyl acetate staple fibers, and the like or mixtures thereof. Suitable cellulosic staple fibers include for example, pulp, thermomechanical pulp, synthetic cellulosic fibers, modified cellulosic fibers, and the like. Cellulosic fibers can be obtained from secondary or recycled sources. Some examples of suitable cellulosic fiber sources include virgin wood fibers, such as thermomechanical, bleached and unbleached softwood and hardwood pulps. Secondary or recycled cellulosic fibers obtained from office waste, newsprint, brown paper stock, paperboard scrap, etc., can also be used. Further, vegetable fibers, such as abaca, flax, milkweed, cotton, modified cotton, cotton linters, can also be used as the cellulosic fibers. In addition, synthetic cellulosic fibers such as, for example, rayon and viscose rayon can be used. Modified cellulosic fibers are generally composed of derivatives of cellulose formed by substitution of appropriate radicals (e.g., carboxyl, alkyl, acetate, nitrate, etc.) for hydroxyl groups along the carbon chain.

One particularly suitable hydroentangled nonwoven web is a nonwoven web composite of polypropylene spunbond fibers, which are substantially continuous fibers, having pulp fibers hydraulically entangled with the spunbond fibers. Another particularly suitable hydroentangled nonwoven web is a nonwoven web composite of polypropylene spunbond fibers having a mixture of cellulosic and non-cellulosic staple fibers hydraulically entangled with the spunbond fibers.

The substrate 15 of the present disclosure can be prepared solely from thermoplastic fibers or can contain both thermoplastic fibers and non-thermoplastic fibers. Generally, when the substrate 15 contains both thermoplastic fibers and non-thermoplastic fibers, the thermoplastic fibers make up from about 10% to about 90%, by weight of the substrate 15. In a particular aspect, the substrate 15 contains between about 10% and about 30%, by weight, thermoplastic fibers.

Generally, a fiber-based substrate 15, such as a nonwoven substrate, will have a basis weight (BW) in the range of about 10 gsm (grams per square meter) to about 200 gsm, depending on the product application. In other aspects, a fiber-based substrate 15, such as a nonwoven substrate, will have a basis weight in the range between about 33 gsm and about 200 gsm. The actual basis weight can be higher than 200 gsm, but for many applications, the basis weight will be in the 12 gsm to 150 gsm range. The materials of the fibers making-up at least a portion of the substrate 15 can essentially be any polymer. Suitable polymers include polyolefins, polyesters, polyamides, polyurethanes, polyvinylchloride, polytetrafluoroethylene, polystyrene, polyethylene terephthalate, biodegradable polymers such as polylactic acid, and copolymers and blends thereof. Suitable polyolefins include polyethylene, for example high density polyethylene, medium density polyethylene, low density polyethylene and linear low density polyethylene; polypropylene, for example isotactic polypropylene, syndiotactic polypropylene, blends of isotactic polypropylene and atactic polypropylene, and blends thereof; polybutylene, that, poly(l-butene) and poly(2-butene); polypentene, for example poly(l-pentene) and poly(2-pentene); poly(3-methyl-1-pentene); poly(4-methyl 1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include polyethylene terephthalate, polytrimethylene terephthalate, polybutylene terephthalate, polytetramethylene terephthalate, polycyclohexylene-1,4-dimethylene terephthalate, and isophthalate copolymers thereof, as well as blends thereof. These polymers can be used to prepare both substantially continuous fibers and staple fibers, in accordance with the present disclosure.

Nonwoven fabrics are used extensively in disposable absorbent products, in which the nonwoven is designed to interact with liquids. Tuning of nonwoven wetting properties allows novel benefits in a disposable absorbent product. For example, a liner with controlled zones of relative hydrophobicity and hydrophilicity allows greater control over the distribution of liquid into the absorbent core.

The present disclosure includes improved personal care products, particularly disposable absorbent articles. Personal care products of the present disclosure include, but are not limited to, feminine hygiene products like sanitary wipes and menses absorbing devices (e.g., sanitary napkins and tampons), infant and child care products such as disposable diapers, absorbent underpants, and training pants, wound dressings such as bandages, incontinent products, products for wiping and absorbing oils and/or organic solvents, and the like.

Disposable absorbent articles such as the feminine care absorbent product, for example, can include a liquid permeable topsheet, a substantially liquid impermeable backsheet joined to the topsheet, and an absorbent core positioned and held between the topsheet and the backsheet. The topsheet is operatively permeable to the liquids that are intended to be held or stored by the absorbent article, and the backsheet can be substantially impermeable or otherwise operatively impermeable to the intended liquids. The absorbent article can also include an additional layer(s). This additional layer(s) can be a liquid intake layer, liquid wicking layers, liquid distribution layers, transfer layers, barrier layers, and the like, as well as combinations thereof. Disposable absorbent articles and the components thereof can operate to provide a body-facing surface (top surface of the topsheet) and a garment-facing surface (back surface of the backsheet). As used herein, the "body-facing" or "bodyside" surface refers to the surface of the topsheet that is disposed toward or placed adjacent to the body of the wearer during ordinary use. The "garment-side surface" refers to the backsheet where the back of the surface is disposed away from the wearer's body and adjacent to the garment of the wearer during ordinary use. Suitable absorbent articles are described in more detail in U.S. Pat. No. 7,632,258.

The fluid permeable topsheet of the present disclosure can be left untreated or can be treated with a superhydrophobic composition that helps to keep fluids from sitting atop the surface that can leave an unpleasant and/or unclean feeling from stains, accumulated debris, or wetness on the surface. The disposable absorbent articles of the present disclosure are particularly adapted to receive fluids having viscoelastic properties, such as menses, mucous, blood products, and feces, among others to reduce stain area, reduce rewet, improve fluid intake, distribution, absorption properties, and decrease leakage.

It will be readily apparent to one skilled in the art based on the disclosure that the products and methods described herein can also be used in combination with numerous absorbent articles designed to absorb fluids other than menses such as runny BM, urine, and the like.

The absorbent articles of the present disclosure include a fluid permeable topsheet that is preferably a nonwoven, body-facing fibrous sheet material. The present disclosure provides an advantage over topsheets including a thermoplastic film because nonwovens are generally softer, cause less sweating and irritation from sweat, and avoid the plastic feel or rustling that is often associated with plastics and films.

EXAMPLES

The following are provided for exemplary purposes to facilitate understanding of the disclosure and should not be construed to limit the disclosure to the examples.

Materials and Procedure

A 25 gsm spunbond nonwoven substrate and a 17 gsm spunbond nonwoven substrate with polypropylene fibers roughly 20 microns in diameter, were patterned via roll-to-roll micro-hot embossing with one of three metal tools. The first metal tool includes an array of pins one micron-wide with a pitch of about two microns, the second metal tool includes cylindrical holes 3 microns in diameter, and the third metal tool includes cylindrical holes 6 microns in diameter. All examples were run at a web speed of 2 m/min. The pins formed a pattern of indentations in the nonwoven fibers, and the cylindrical holes patterns formed hemispherical protrusions from the fibers. After embossing, the fabric was loosened by hand by pulling in several directions. Several runs were performed with different pressure roll materials and varying the number of cycles of embossing and loosening. See Table 1 for a description of the examples. Contact angle of purified water was measured using a KRÜSS Mobile Surface Analyzer with a 1 μL droplet size. Water was purified to a resistance of 18.2 MΩ·cm. A droplet is automatically dispensed onto the surface, an image of the droplet is acquired from the side, and Kruss Advance drop shape analysis software is used to measure the contact angle on the left and right sides of the droplet. The reported contact angle is an average of measurements from at least three droplets.

or four fiber regions containing patterns were selected and the 3D surface area, 2D projected area, and the ratio of the two were calculated by the VK Analyzer software from Keyence. Values in the table are average values.

Pattern coverage was identified using image analysis. Coverage=# of pixels identified as containing "pattern"/# of pixels identified as containing "fiber." Images of the patterned side of embossed nonwovens were acquired from a Keyence laser confocal/optical microscope with a 20× objective lens. Images had sufficient detail to clearly identify patterned versus un-patterned regions of the fibers. Images were acquired from the normal direction relative to the surface. Roughly, the top three fiber layers are clear in the images, while fibers at increasing depth are less clearly captured.

"Pattern" regions were identified using a "convolve" edge detection method in ImageJ, an open source detection software program developed by NIH (version 1.50b), to identify high contrast areas of the image. "Fiber" regions were identified using an intensity threshold combined with the "pattern" high contrast areas (to make sure all "pattern" pixels were also counted as "fiber" pixels).

Figure 3:
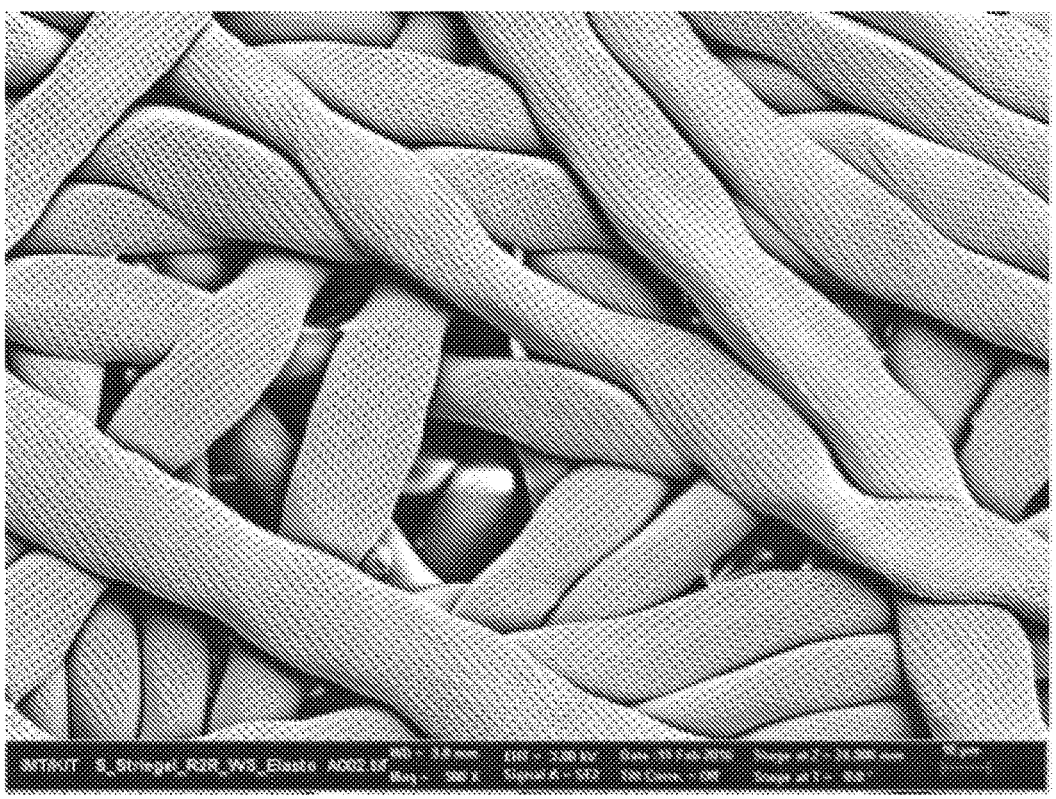
FIG. 3 is a photographic scanning electron microscope (SEM) illustration of a nonwoven substrate produced using a silicone backing material in the process of FIG. 1.

It was determined that the soft, rubbery ELASTOSIL silicone (Wacker Chemie; Elastosil M4601 A+B; Part A: Part B; 9:1) surface did not prevent the crushing of the web (see FIG. 3). Conversely, the felt (uncarbonized wool felt, 4

TABLE 1

| Code | BW (gsm) | Embossing pattern | Embossing steps | Temp (° C.) | P (N) | Contact Angle (deg) | Density (g/cc) | Pattern roughness | Pattern Coverage |
| --- | --- | --- | --- | --- | --- | --- | --- | --- | --- |
| 1 Control | 25 | — | 0 | — | — | 122.7 | 0.067 | 1.06* | 0.05* |
| 2 Control | 17 | — | 0 | — | — | 128.03 | 0.074 | Not tested | Not tested |
| 3 | 25 | 1 μm pins | 3 | 91 | 5800 | 133.4 | 0.084 | 3.76 | 0.75 |
| 4 | 25 | 1 μm pins | 4 | 91 | 6200 | 134.2 | 0.114 | 3.59 | 0.77 |
| 5 | 25 | 1 μm pins | 1 | 92 | 3600 | 131.0 | 0.077 | 3.37 | 0.26 |
| 6 | 25 | 1 μm pins | 1 | 89 | 4200 | 129.4 | 0.075 | Not tested | Not tested |
| 7 | 25 | 1 μm pins | 1 | 89 | 8000 | 131.2 | 0.100 | Not tested | Not tested |
| 8 | 17 | 3 μm holes | 1 | 93 | 9000 | 123.9 | 0.143 | 1.48 | 0.57 |
| 9 | 17 | 3 μm holes | 3 | 93 | 9000 | 129.0 | 0.110 | 1.76 | 0.71 |
| 10 | 17 | 6 μm holes | 1 | 93 | 9000 | 124.2 | 0.127 | 3.03 | 0.36 |
| 11 | 17 | 6 μm holes | 4 | 93 | 9000 | 129.7 | 0.116 | 1.38 | 0.48 |

Results and Discussion

It was discovered that an increased contact angle occurs when three conditions are met from the embossing process. First, fibers are embossed with a pattern that confers a high pattern roughness. Second, the pattern covers a large fraction of the exposed sheet surface, leaving little un-patterned fiber surface. Finally, after embossing the nonwoven sheet remains lofty, retaining a low density.

For example, increased contact angle samples had a density below 0.12 g/cc, a pattern roughness above 1.5, and a pattern coverage above 20%. For examples with a density less than 0.12 g/cc, the contact angle (in degrees) was described by the expression 121.5+6.7×(% Pattern Coverage)+2.0×(Pattern Roughness), with an $R^2$ of 0.9 and a p-value of 0.03. Caliper was measured using a micrometer with 50-mm diameter platen and a pressure of 0.05 psi. Density was calculated from caliper and nominal basis weight, and bulk inverse of density.

Figure 2:
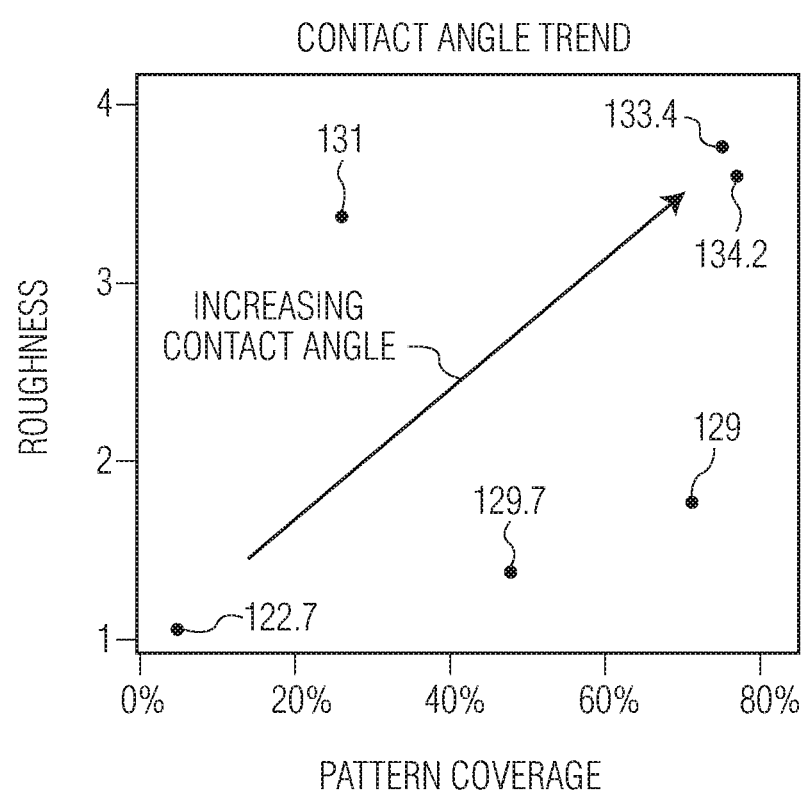
FIG. 2 graphically illustrates the relationship between contact angle to surface roughness and pattern coverage on a material provided using the process of FIG. 1.
Figure 4:
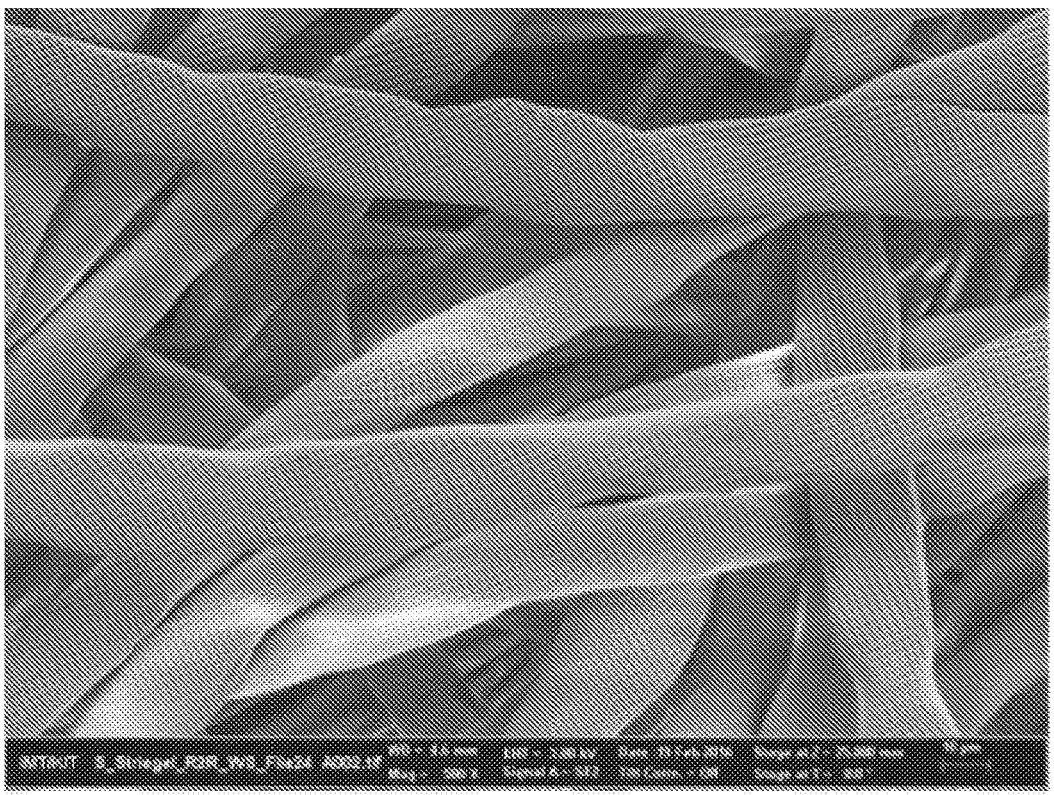
FIG. 4 is a photographic SEM illustration of a nonwoven substrate produced using a felt backing material and six cycles of embossing in the process of FIG. 1.
Figure 5:
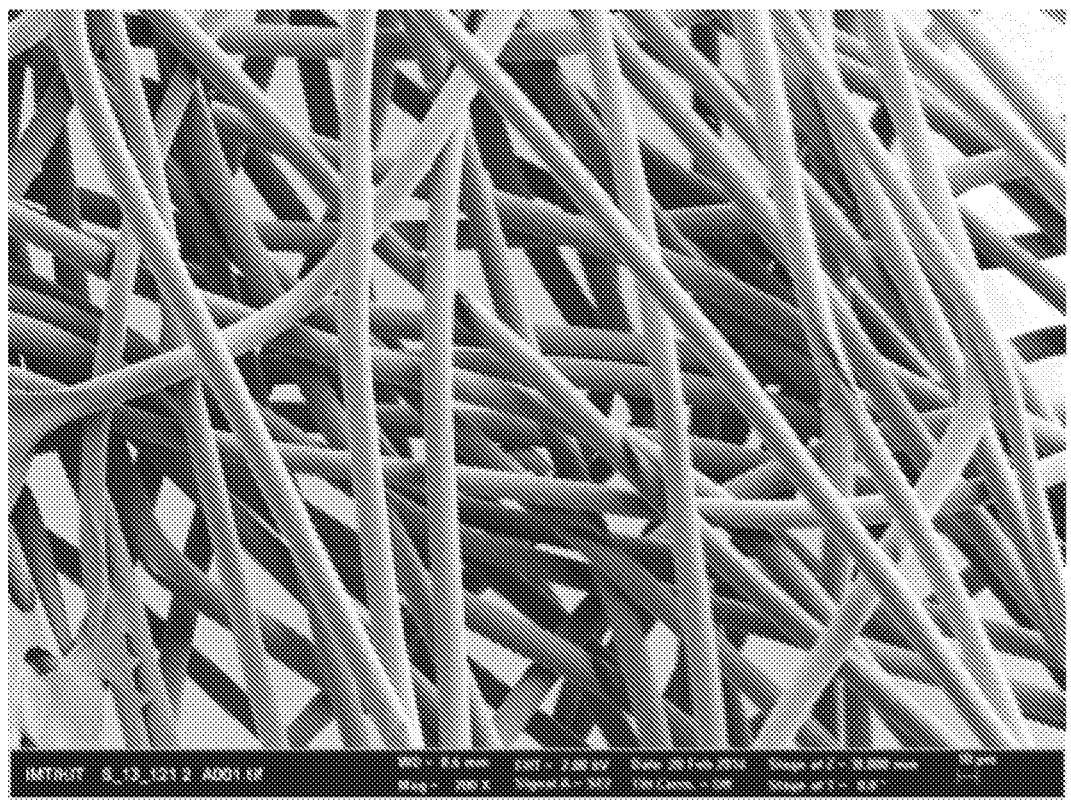
FIG. 5 is a photographic SEM illustration of a control nonwoven substrate without the embossing process of FIG. 1.

Surface roughness was defined as the 3D surface area/2D projected area. Surfaces were characterized using Keyence laser confocal microscope, using a 50× or 100× objective lens sufficient to show the embossed patterns in detail. Three mm material thickness, 0.375 g/cm$^3$) pressure roll coating was effective in preventing the crushing of the web (see FIG. 4). Contact angle increased with each embossing cycle (other than the first) to a maximum of 134.2 degrees (see FIG. 2) based on measurable material attributes. After embossing/loosening cycles, the fiber maintained an open structure without fusing fibers or significantly stiffening the sheet.

Dynamic contact angles were measured for all substrates on glass slides to better understand the role of pattern size and the number of embossing cycles. For any hydrophobic surface, the sessile contact angle is generally considered limited for understanding how mobile droplets are expected to be when introduced to the surface.

In a first particular aspect, a nonwoven substrate includes individual fibers each having a fiber surface and a fiber diameter, wherein a portion of the individual fibers include a micro-embossed pattern, and wherein the micro-embossed pattern includes pattern elements equal to or smaller than the fiber diameter.

A second particular aspect includes the first particular aspect, wherein the pattern elements are each 10 microns or less.

A third particular aspect includes the first and/or second aspect, wherein the pattern elements are recessed into and/or extend out of the fiber surface.

A fourth particular aspect includes one or more of aspects 1-3, wherein a contact angle of the nonwoven substrate is elevated by 5 or more degrees when compared to the same nonwoven substrate without a micro-embossed pattern.

A fifth particular aspect includes one or more of aspects 1-4, wherein a contact angle of the nonwoven substrate is elevated by 10 or more degrees when compared to the same nonwoven substrate without a micro-embossed pattern.

A sixth particular aspect includes one or more of aspects 1-5, wherein the nonwoven substrate has a contact angle greater than 128 degrees.

A seventh particular aspect includes one or more of aspects 1-6, wherein the nonwoven substrate includes a thermoplastic polymer.

An eighth particular aspect includes one or more of aspects 1-7, wherein the thermoplastic polymer includes polypropylene or polyethylene.

A ninth particular aspect includes one or more of aspects 1-8, wherein the micro-embossed pattern has a pattern roughness, and wherein the pattern roughness is greater than 1.5.

A tenth particular aspect includes one or more of aspects 1-9, the nonwoven substrate having a substrate density of less than 0.12 g/cc.

In an eleventh particular aspect, a nonwoven substrate includes individual fibers each having a fiber surface and a fiber diameter, wherein a portion of the individual fibers include a micro-embossed pattern, wherein the micro-embossed pattern includes pattern elements equal to or smaller than the fiber diameter, wherein the pattern elements are recessed into and/or extend out of the fiber surface, and wherein the nonwoven substrate includes polypropylene or polyethylene.

A twelfth particular aspect includes the eleventh particular aspect, wherein the pattern elements are 10 microns or less.

A thirteenth particular aspect includes the eleventh and/or twelfth aspect, wherein a contact angle of the nonwoven substrate is elevated by 5 or more degrees when compared to the same nonwoven substrate without a micro-embossed pattern.

A fourteenth particular includes one or more of aspects 11-13, wherein a contact angle of the nonwoven substrate is elevated by 10 or more degrees when compared to the same nonwoven substrate without a micro-embossed pattern.

A fifteenth particular aspect includes one or more of aspects 11-14, wherein the micro-embossed pattern has a pattern roughness, and wherein the pattern roughness is greater than 1.5.

A sixteenth particular aspect includes one or more of aspects 11-15, the nonwoven substrate having a substrate density of less than 0.12 g/cc.

In a seventeenth particular aspect, a disposable absorbent article includes a nonwoven substrate having individual fibers each having a fiber surface and a fiber diameter, wherein a portion of the individual fibers include a micro-embossed pattern, and wherein the micro-embossed pattern includes pattern elements equal to or smaller than the fiber diameter.

An eighteenth particular aspect includes the seventeenth aspect, wherein the disposable absorbent article is a feminine hygiene product, an infant care product, a child care product, an incontinence product, or a wound dressing.

A nineteenth particular aspect includes the seventeenth and/or eighteenth aspects, wherein a contact angle of the nonwoven substrate is elevated by 5 or more degrees when compared to the same nonwoven substrate without a micro-embossed pattern.

A twentieth particular aspect includes one or more of aspects 17-19, wherein a contact angle of the nonwoven substrate is elevated by 10 or more degrees when compared to the same nonwoven substrate without a micro-embossed pattern.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed:

1. A nonwoven substrate comprising individual fibers each having a fiber surface and a fiber diameter, wherein a portion of the individual fibers include a micro-embossed pattern, and wherein the micro-embossed pattern includes pattern elements equal to or smaller than the fiber diameter, wherein the micro-embossed pattern has a pattern roughness, and wherein the pattern roughness is greater than 1.5, the nonwoven substrate having a substrate density of less than 0.12 g/cc, and wherein the nonwoven substrate has a pattern coverage of at least 20% based on the projected fiber surface area visible from above.

2. The nonwoven substrate of claim 1, wherein the pattern elements are each 10 microns or less.

3. The nonwoven substrate of claim 1, wherein the pattern elements are recessed into and/or extend out of the fiber surface.

4. The nonwoven substrate of claim 1, wherein a contact angle of the nonwoven substrate is elevated by 5 or more degrees when compared to the same nonwoven substrate without a micro-embossed pattern.

5. The nonwoven substrate of claim 1, wherein a contact angle of the nonwoven substrate is elevated by 10 or more degrees when compared to the same nonwoven substrate without a micro-embossed pattern.

6. The nonwoven substrate of claim 1, wherein the nonwoven substrate has a contact angle greater than 128 degrees.

7. The nonwoven substrate of claim 1, wherein the nonwoven substrate includes a thermoplastic polymer.

8. The nonwoven substrate of claim 7, wherein the thermoplastic polymer includes polypropylene or polyethylene.

9. A nonwoven substrate comprising individual fibers each having a fiber surface and a fiber diameter, wherein a portion of the individual fibers include a micro-embossed pattern, wherein the micro-embossed pattern includes pattern elements equal to or smaller than the fiber diameter, wherein the pattern elements are recessed into and/or extend out of the fiber surface, and wherein the nonwoven substrate includes polypropylene or polyethylene, wherein the micro-embossed pattern has a pattern roughness, and wherein the pattern roughness is greater than 1.5, the nonwoven substrate having a substrate density of less than 0.12 g/cc, and wherein the nonwoven substrate has a pattern coverage of at least 20% based on the projected fiber surface area visible from above.

10. The nonwoven substrate of claim 9, wherein the pattern elements are 10 microns or less.

11. The nonwoven substrate of claim 9, wherein a contact angle of the nonwoven substrate is elevated by 5 or more degrees when compared to the same nonwoven substrate without a micro-embossed pattern.

12. The nonwoven substrate of claim 9, wherein a contact angle of the nonwoven substrate is elevated by 10 or more degrees when compared to the same nonwoven substrate without a micro-embossed pattern.

13. A disposable absorbent article comprising a nonwoven substrate having individual fibers each having a fiber surface and a fiber diameter, wherein a portion of the individual fibers include a micro-embossed pattern, and wherein the micro-embossed pattern includes pattern elements equal to or smaller than the fiber diameter, wherein the micro-embossed pattern has a pattern roughness, and wherein the pattern roughness is greater than 1.5, the nonwoven substrate having a substrate density of less than 0.12 g/cc, and wherein the nonwoven substrate has a pattern coverage of at least 20% based on the projected fiber surface area visible from above.

14. The disposable absorbent article of claim 13, wherein the disposable absorbent article is a feminine hygiene product, an infant care product, a child care product, an incontinence product, or a wound dressing.

15. The disposable absorbent article of claim 13, wherein a contact angle of the nonwoven substrate is elevated by 5 or more degrees when compared to the same nonwoven substrate without a micro-embossed pattern.

16. The disposable absorbent article of claim 13, wherein a contact angle of the nonwoven substrate is elevated by 10 or more degrees when compared to the same nonwoven substrate without a micro-embossed pattern.

* * * * *